United States Patent
Klimasauskas et al.

(10) Patent No.: US 11,008,605 B2
(45) Date of Patent: May 18, 2021

(54) ANALYSIS OF SINGLE-STRANDED RNA

(71) Applicant: VILNIUS UNIVERSITY, Vilnius (LT)

(72) Inventors: Saulius Klimasauskas, Vilnius (LT); Giedrius Vilkaitis, Vilnius (LT); Milda Mickute, Vilnius (LT)

(73) Assignee: Vilnius University, Vilnius (LT)

( * ) Notice: Subject to any disclaimer, the term of this patent is extended or adjusted under 35 U.S.C. 154(b) by 93 days.

(21) Appl. No.: 15/559,689

(22) PCT Filed: Mar. 18, 2016

(86) PCT No.: PCT/LT2016/000002
§ 371 (c)(1),
(2) Date: Sep. 19, 2017

(87) PCT Pub. No.: WO2016/148556
PCT Pub. Date: Sep. 22, 2016

(65) Prior Publication Data
US 2018/0251814 A1    Sep. 6, 2018

(30) Foreign Application Priority Data

Mar. 19, 2015  (LT) ..................................... 2015019

(51) Int. Cl.
| | | |
|---|---|---|
| *C12Q 1/68* | (2018.01) | |
| *C12Q 1/6806* | (2018.01) | |
| *C12Q 1/6853* | (2018.01) | |
| *C12Q 1/6876* | (2018.01) | |

(52) U.S. Cl.
CPC ......... *C12Q 1/6806* (2013.01); *C12Q 1/6853* (2013.01); *C12Q 1/6876* (2013.01); *C12Q 2521/125* (2013.01); *C12Q 2563/137* (2013.01)

(58) Field of Classification Search
None
See application file for complete search history.

(56) References Cited

U.S. PATENT DOCUMENTS 8,008,007 B2 * 8/2011 Weinhold ............... C07H 21/00
435/6.11

FOREIGN PATENT DOCUMENTS

WO    2013187745 A1    12/2013

OTHER PUBLICATIONS

Chio Mui Chan, et al., Structural and biochemical insights into 2'-O-methylation at the 3'-terminal nucleotide of RNA by Hen1, Proceedings of the National Academy of Sciences (PNAS), Oct. 20, 2009, pp. 17699-17704, vol. 106, No. 42.

Michael D. Horwich, et al., The *Drosophila* RNA Methyltransferase, DmHen1, Modifies Germline piRNAs and Single-Stranded siRNAs in RISC, Current Biology, Jul. 17, 2007, pp. 1265-1272, vol. 17, Elsevier Ltd.

Kuniaki Saito, et al., Pimet, the *Drosophila* homolog of HEN1, mediates 2'-O-methylation of Piwi-interacting RNAs at their 3' ends, Genes & Development, pp. 1603-1608, vol. 21, Cold Spring Harbor Laboratory Press.

Jul. 21, 2016, International Search Report issued for related International Application No. PCT/LT2016/000002.

* cited by examiner

*Primary Examiner* — James Martinell
(74) *Attorney, Agent, or Firm* — AAA Law

(57) ABSTRACT

Provided is a method for modifying a ssRNA at the 3' end, the method including contacting the strand with a ssRNA 2'-O-methyltransferase in the presence of a co-factor, under conditions which allow for the transfer by the ssRNA 2'-O-methyltransferase of a part of the co-factor onto the 3' end of the ssRNA to form a modified ssRNA, wherein the ssRNA bears 2'-OH group at 3' terminal nucleotide and wherein the part of the co-factor transferred includes a reporter group or a functional group.

18 Claims, 7 Drawing Sheets

Specification includes a Sequence Listing.

SEQUENCE LISTING

<160> NUMBER OF SEQ ID NOS: 4

<210> SEQ ID NO 1
<211> LENGTH: 393
<212> TYPE: PRT
<213> ORGANISM: Homo sapiens

<400> SEQUENCE: 1

```
Met Glu Glu Asn Asn Leu Gln Cys Ser Ser Val Val Asp Gly Asn Phe
1               5                   10                  15

Glu Glu Val Pro Arg Glu Thr Ala Ile Gln Phe Lys Pro Pro Leu Tyr
            20                  25                  30

Arg Gln Arg Tyr Gln Phe Val Lys Asn Leu Val Asp Gln His Glu Pro
        35                  40                  45

Lys Lys Val Ala Asp Leu Gly Cys Gly Asp Thr Ser Leu Leu Arg Leu
    50                  55                  60

Leu Lys Val Asn Pro Cys Ile Glu Leu Leu Val Gly Val Asp Ile Asn
65                  70                  75                  80

Glu Asp Lys Leu Arg Trp Arg Gly Asp Ser Leu Ala Pro Phe Leu Gly
            85                  90                  95

Asp Phe Leu Lys Pro Arg Asp Leu Asn Leu Thr Ile Thr Leu Tyr His
            100                 105                 110

Gly Ser Val Val Glu Arg Asp Ser Arg Leu Leu Gly Phe Asp Leu Ile
        115                 120                 125

Thr Cys Ile Glu Leu Ile Glu His Leu Asp Ser Gly Asp Leu Ala Arg
    130                 135                 140
```

Phe Pro Glu Val Val Phe Gly Tyr Leu Ser Pro Ser Met Ile Val Ile
145                 150                 155                 160

Ser Thr Pro Asn Ser Glu Phe Asn Pro Leu Phe Pro Ser Val Thr Leu
            165                 170                 175

Arg Asp Ser Asp His Lys Phe Glu Trp Thr Arg Met Glu Phe Gln Thr
            180                 185                 190

Trp Ala Leu Tyr Val Ala Asn Arg Tyr Asp Tyr Ser Val Glu Phe Thr
            195                 200                 205

Gly Val Gly Glu Pro Pro Gly Ala Glu Asn Val Gly Tyr Cys Thr
            210                 215                 220

Gln Ile Gly Ile Phe Arg Lys Asn Gly Gly Lys Ala Thr Glu Ser Cys
225                 230                 235                 240

Leu Ser Glu Gln His Asp Gln His Val Tyr Lys Ala Val Phe Thr Thr
            245                 250                 255

Ser Tyr Pro Ser Leu Gln Gln Glu Arg Phe Phe Lys Leu Val Leu Val
            260                 265                 270

Asn Glu Val Ser Gln Gln Val Gly Ser Leu Arg Val Ser His Leu Pro
            275                 280                 285

Arg Arg Lys Glu Gln Ala Gly Glu Arg Gly Asp Lys Pro Lys Asp Ile
            290                 295                 300

Gly Gly Ser Lys Ala Pro Val Pro Cys Phe Gly Pro Val Phe Thr Glu
305                 310                 315                 320

Val Glu Lys Ala Lys Ile Glu Asn Ser Pro Thr Pro Phe Cys Val Gly
            325                 330                 335

Asp Lys Phe Phe Val Pro Leu Gln Arg Leu Leu Ala Tyr Pro Lys Leu
            340                 345                 350

Asn Arg Leu Cys Ala Asn Glu Glu Met Met Arg Ser Val Ile Ala Asp
            355                 360                 365

Ser Ile Pro Leu Ser Ser Asp Gly Ser Ala Val Val Ala Asp Leu Arg
            370                 375                 380

Asn Tyr Phe Asp Glu Gln Phe Glu Phe
385                 390

<210> SEQ ID NO 2
<211> LENGTH: 391
<212> TYPE: PRT
<213> ORGANISM: Drosophila melanogaster

<400> SEQUENCE: 2

Met Phe Ser His Lys Phe Ile Cys Gly Ser Leu Thr Lys Met Thr Glu
1               5                   10                  15

Thr Gly Ile Thr Phe Asp Pro Pro Val Tyr Glu Gln Arg Tyr Cys Ala
            20                  25                  30

Thr Ile Gln Ile Leu Glu Asp Ala Arg Trp Lys Asp Gln Ile Lys Lys
            35                  40                  45

Val Val Glu Phe Gly Cys Ala Glu Met Arg Phe Phe Gln Leu Met Arg
            50                  55                  60

Arg Ile Glu Thr Ile Glu His Ile Gly Leu Val Asp Ile Asp Lys Ser
65                  70                  75                  80

Leu Leu Met Arg Asn Leu Thr Ser Val Asn Pro Leu Val Ser Asp Tyr
            85                  90                  95

Ile Arg Ser Arg Ala Ser Pro Leu Lys Val Gln Ile Leu Gln Gly Asn
            100                 105                 110

Val Ala Asp Ser Ser Glu Glu Leu Arg Asp Thr Asp Ala Val Ile Ala
            115                 120                 125

Ile Glu Leu Ile Glu His Val Tyr Asp Asp Val Leu Ala Lys Ile Pro
    130                 135                 140

Val Asn Ile Phe Gly Phe Met Gln Pro Lys Leu Val Val Phe Ser Thr
145                 150                 155                 160

Pro Asn Ser Asp Phe Asn Val Ile Phe Thr Arg Phe Asn Pro Leu Leu
                165                 170                 175

Pro Asn Gly Phe Arg His Glu Asp His Lys Phe Glu Trp Ser Arg Asp
                180                 185                 190

Glu Phe Lys Asn Trp Cys Leu Gly Ile Val Glu Lys Tyr Pro Asn Tyr
            195                 200                 205

Met Phe Ser Leu Thr Gly Val Gly Asn Pro Pro Lys Glu Tyr Glu Ser
210                 215                 220

Val Gly Pro Val Ser Gln Ile Ala Ile Phe Val Arg Lys Asp Met Leu
225                 230                 235                 240

Glu Met Gln Leu Val Asn Pro Leu Val Ser Lys Pro Asn Ile Asp Lys
                245                 250                 255

Glu Ser Ile Pro Tyr Lys Leu Ile His Thr Val Glu Tyr Pro Phe Tyr
                260                 265                 270

Val Asp Thr Arg Thr Glu Lys Glu Lys Leu Trp Thr Glu Val Gln Ile
            275                 280                 285

Glu Leu Gln Arg Phe Lys Arg Gln Phe Glu Ser Ser Glu Ile Glu Glu
290                 295                 300

Gly Thr Tyr Gln Asp Thr Cys Asn Met Pro Ile Ala Phe Leu Leu Asp
305                 310                 315                 320

Arg Leu Glu His Val Gly Ala Thr Lys Glu Arg Ile Glu Glu Leu Leu
                325                 330                 335

Leu Glu Asn Asn Leu Thr Val Glu Asn Glu Cys Val Leu Ile Val Ser
                340                 345                 350

Ser Asp Gln Glu Ser Glu Trp Ser Asp Pro Tyr Lys Phe Ser Asp Arg
            355                 360                 365

Ser Ser Gln Asp Asp Ala Leu Val Asp Gln Glu Gln Glu Glu Glu Arg
370                 375                 380

Trp Asp Gln Gly Pro Glu Ser
385                 390

<210> SEQ ID NO 3
<211> LENGTH: 22
<212> TYPE: RNA
<213> ORGANISM: Artificial Sequence
<220> FEATURE:
<223> OTHER INFORMATION: synthesized

<400> SEQUENCE: 3
uucgcuugca gagagaaauc ac                                          22

<210> SEQ ID NO 4
<211> LENGTH: 23
<212> TYPE: RNA
<213> ORGANISM: Artificial Sequence
<220> FEATURE:
<223> OTHER INFORMATION: synthesized

<400> SEQUENCE: 4
uuaacgcuug cagagagaau cac                                         23

ANALYSIS OF SINGLE-STRANDED RNA

This application contains sequence listing that has been submitted as an ASCII file named 9051-1029 US SEQ ID_ST25, the date of creation Sep. 24, 2019, and the size of the ASCII text file in bytes is 8,192 bytes.

FIELD OF THE INVENTION

The present invention relates to methods of labelling RNA molecules, and to the use of these methods in the analysis of single-stranded RNA (ssRNA) molecules in various biological samples.

BACKGROUND TO THE INVENTION

RNAs that are not translated into proteins, non-coding RNAs, are both abundant and important in eukaryotic and prokaryotic organisms (Lalaouna et al., (2013) Biochim Biophys Acta. 1829, 742-747).

Small non-coding RNAs, such as miRNAs, siRNAs and piRNAs, all about 21-32 nt in length, are one of the main and crucial posttranscriptional gene regulators in eukaryotes (Ghildiyal and Zamore, (2009) Nat Rev Genet. 10, 94-108). Being expressed under tight spatial and temporal control, small non-coding RNAs influence all aspects of organism's biology, including its development, metabolism and response to environmental conditions (Planell-Saguer and Rodicio, (2011) Anal Chim Acta. 699, 134-152). As a result, even minor deregulation of their expression ends up in pathology, such as cancer, or is an indicator of it (Jansson and Lund, (2012) Mol Oncol., 6, 590-610). In humans, the possibility to use small RNAs, in particular miRNAs, to monitor the progression of disease and its treatment is well understood and already applied in some cases (Wang et al., (2013) Med Hypotheses. 81, 41-43; Zhao et al., (2013) Oncol. Rep. 30, 276-84). And even greater potential for use as non-invasive biomarkers is seen in circulating miRNAs found as stable complexes in human bodily fluids (Zen and Zhang, (2012) Med Res Rev. 32, 326-348).

The importance of another class of small non-coding RNAs, bacterial small regulatory RNAs (sRNAs, 50-400 nt), became apparent only recently due to the intensive research in prokaryote genetics during the last decade (Lalaouna et al., (2013) Biochim Biophys Acta. 1829, 742-727). As major class of post-transcriptional regulators, sRNAs control crucial physiological processes such as carbon metabolism or membrane homeostasis, as well as respond to growth face and environmental stressors (Mandin and Guillier, (2013) Curr Opin Microbiol. 16, 125-132; Burke et al., (2014) J Bacteriol. 196, 3756-3767). As new studies highlight the importance of sRNAs for bacterial virulence, their identification and characterization is potentially beneficial for development of next-generation antibiotics (Harris et al., (2013) Virulence 15, 785-795).

The majority of current methods for the identification and analysis of known small single-stranded RNA (ssRNA) species rely on their hybridization with oligonucleotide probes or amplification. Most often approaches based on Northern-blotting, oligonucleotide microarray technologies or reverse-transcription quantitative polymerase chain reaction (RT-qPCR) are used. However, all these strategies have inherent technical shortcomings and limitations as follows:

1. Northern-blotting measures the target RNA directly hybridized with a labeled oligonucleotide immobilized on a solid (nitrocellulose) membrane following electrophoretic separation on a polyacrylamide gel. It is relatively inexpensive and requires very basic laboratory facilities. However this method often suffers from inefficient transfer to the membrane and immobilization of short RNAs. Since no target amplification is possible, relatively large amounts of input RNA sample are required for analysis.

2. Although microarray hybridization offers highly parallel analysis with multiple probes, it requires prolonged extensive experimental time, expensive equipment, advanced professional skills and large quantities of input sample. What is more, sample labeling is often laborious and prone to biases, such as DNA inclusion. Since the methodologies are not standardized, there are significant experimental variations between different manufacturers and laboratories, often leading to considerable inconsistencies in published results (Sato et al., (2009) PLoS ONE 4, e5540).

3. RT-qPCR operates with small amounts of starting material (nanograms of total RNA). However this time-consuming and technically complicated approach is difficult to adapt for routine clinical testing (Planell-Saguer and Rodicio, (2013) Clin Biochem. 46, 869-878). The short length of small RNAs hampers their amplification and analysis. Since the technique is not specific for the type (RNA vs. DNA) of nucleic acid, there is a high probability of contamination with genomic DNA.

Current approaches used for the discovery of new species of non-coding RNAs are based on cloning certain fractions of cellular RNA followed by their massive parallel sequencing. Such approaches share the following disadvantages:

1. The enrichment for cellular small single-stranded RNAs is solely based on size-separation by denaturing polyacrylamide gel electrophoresis of total cellular RNAs. The method is thus unable to discriminate between ssRNA and short DNA contamination. This serious drawback impairs the discovery and proper analysis of new ssRNAs. In addition, at 3' end unprotected single-stranded RNAs are very sensitive to degradation by contaminating nucleases, and certain ssRNA species may be completely lost during prolonged handling inherent for electrophoretic size-separation.

2. Adapter sequences need to be attached to the 3'-termini of small RNAs by T4 RNA ligase1 or 2 for RT-PCR and amplification. Since both enzymes exhibit a high degree of sequence and structure bias, certain cellular small RNAs are often underrepresented or lost completely during cloning. Even though primed, but also underrepresented are at terminal 3' nucleotide 2'-O-methylated RNAs. This is because T4 RNA ligases accept 2'-O-methylated RNA substrates with ~1.5 fold lower efficiency compared to 2'-OH substrates (Munafo and Robb, (2010) RNA 16, 2537-2552). As both T4 RNA ligases are able to use 5'-P DNA ends as donors and ligase 1 also uses 3'-OH DNA as acceptor, DNA contamination becomes inevitable (Zhuang et al., (2012) *J Nucleic Acids*., epub June 20). Another drawback using RNA ligases for 3'-adapter attachment is the circularization of analyzed RNA as well as adapter—ones circularized both molecules are lost from further analysis (Hafner et al., (2011) RNA 17, 1697-1712). Even though sequencing approaches are composed of many enzymatic steps, a multitude of studies have shown that adapter ligation is the main cause of expression profile biases which can appear as difference of multiple orders of magnitude between over and under-expressed small RNAs (Raabe et al., (2013) *Nucleic Acids Res.* 42, 1414-1426).

It is the aim of the present invention to solve the above shortcomings of the prior art described above.

SUMMARY OF THE INVENTION

In a first aspect the present invention provides a method for modifying ssRNA at the 3' end, said method comprising contacting the strand with a ssRNA 2'-O-methyltransferase in the presence of a co-factor, under conditions which allow for the transfer by the ssRNA 2'-O-methyltransferase of a part of the co-factor onto the 3' end of the ssRNA to form a modified ssRNA, wherein the ssRNA bears 2'-OH group at 3' terminal nucleotide and wherein the part of the co-factor transferred comprises a reporter group or a functional group.

The inventors have surprisingly found that ssRNA 2'-O-methyltransferases from human and *Drosophila melanogaster* can direct the transfer of an extended sulfonium-bound groups from S-adenosyl-L-methionine analogs to natural ssRNA substrates from a virus, a microorganism, a plant or an animal (including human) as well as synthetic ssRNAs of various length. In one embodiment the extended sulfonium-bound group comprises a reporter group that can be used directly for analysis of the ssRNA. In an alternative embodiment the extended sulfonium-bound group that is transferred comprises a functional group which can be utilized in a second step to bind a reporter group to the ssRNA.

Accordingly, the present invention also provides a method for analyzing ssRNAs present in various biological samples, said method comprising:

(a) attaching a reporter group to the 3' end of ssRNA in the biological sample using the method, according to the first aspect of the invention;

(b) analysing the reporter group attached to the ssRNA, according to the second aspect of the invention.

Still further the present invention provides a kit for use in labeling of ssRNA comprising in separate containers (a) a co-factor comprising a reporter group or a functional group; and (b) ssRNA 2'-O-methyltransferases capable of transferring the reporter group or the functional group onto the ssRNA.

The methods according to the present invention can be used for the exploration and analysis of small RNAs transcriptome and the discovery of new species of small non-coding RNAs, circular RNAs and any other ssRNAs in biological samples of organisms from all life domains, with no exception to humans.

In particular, the methods of present invention are advantageous because of high specificity of the ssRNA 2'-O-methyltransferases to one type of nucleic acid, namely RNA, and its terminal 2'-OH group. This eliminates the possibility of undesired labeling of RNA degradation products, carrying 2'-P, 3'-P or 2'3'-cyclic P termini, as well as DNA, with the last one enabling RNA analysis in nucleic acid mixture.

What is more, the created methods enable the modification of substrates of various length by ssRNA 2'-O-methyltransferases and makes it possible to analyze ssRNAs from organisms as different as animals and bacterial pathogens where ssRNA length varies from 21-32 to 50-400 nt or even to 81000 nt.

In addition, since the present methods allow labeling of only 3' unmodified RNAs, they are great tools for pathology identification in organisms, tissues or specific cell lines there ssRNAs are usually 3'-methylated, such as plants or animal germline cells carrying piRNAs.

In view of the above, the methods of the present invention provide an advantageous way of analyzing the entire pull of single stranded RNAs in biological samples.

DESCRIPTION OF FIGURES

The invention will be described in more detail with reference to the Figures in which.

DETAILED DESCRIPTION OF THE INVENTION

Figure 1:
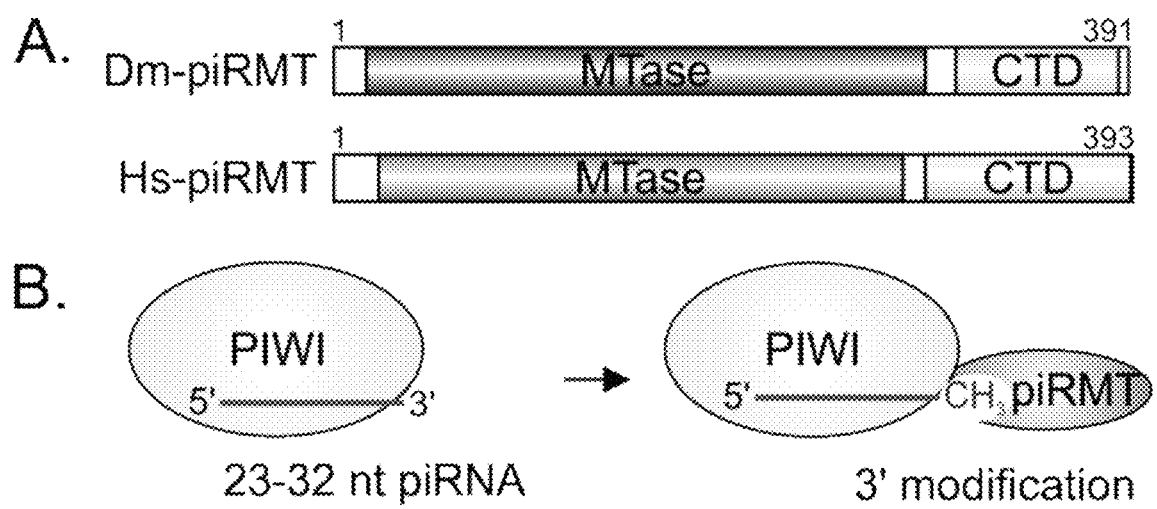
FIG. 1 Schematic representation of *Drosophila melanogaster* and *Homo sapiens* ssRNA 2'-O-methyltransferases, Dm-piRMT and Hs-piRMT, respectively (A), together with the illustration of their natural role in piRNA modification (B). A. Dm-piRMT and Hs-piRMT are 391 and 393 aa. long proteins with methyltransferase (MTase) domain at N termini and about 100 aa long C-terminal domain (CTD) of unknown function. B. PIWI protein bound piRNAs are modified at their 3' termini by ssRNA 2'-O-methyltransferase this being the last step of piRNA biogenesis.

As indicated above the present invention provides, in a first aspect, a method for modifying a single-stranded RNA at the 3' end, said method comprising contacting the strand with a ssRNA 2'-O-methyltransferase in the presence of a co-factor, under conditions which allow for the transfer by the ssRNA 2'-O-methyltransferase of a part of the co-factor onto the 3' end of the single-stranded RNA to form a modified RNA, wherein the part of the co-factor transferred comprises a reporter group or a functional group.

Enzyme

The present inventors have surprisingly found that ssRNA 2'-O-methyltransferase enzymes are able to transfer a reporter group or a functional group from a co-factor onto ssRNA. In particular this ssRNA is not the enzymes' natural substrate, that it is not human's or D. melanogaster's piRNA, and is, preferably, up to 2.5 times longer than it. Using Co$^{2+}$ as metal cofactor, high efficiency of modification reaction and uniformity towards different terminal nucleotides is achieved.

The ssRNA 2'-O-methyltransferases modify exceptionally ssRNAs (Saito et al., (2007) Genes Dev. 21, 1603-1608). Mainly this is because their lack double-stranded RNA binding domain, contrary to their plant homologs (Huang, (2012) Biochemistry 51, 4087-4095) and, probably, differs in characteristics of methyltransferase domain (Vilkaitis et al., (2010) RNA 16, 1935-1942). It is proposed, that the length of ssRNA 2'-O-methyltransferase's substrate is determined during the interaction with enzyme's partners, PIWI proteins (Horwich et al., (2007) Curr Biol. 17, 1265-1272).

As ssRNA 2'-O-methyltransferase homologs use both Mn$^{2+}$ and Mg$^{2+}$ ions as metal cofactors, it is shown that Hs-piRMT modifies RNA in a presence of Mn$^{2+}$, although to seemingly low levels (Huang, (2012) Biochemistry 51, 4087-4095; Chan et al., (2009) Proc Natl Acad Sci USA. 106, 17699-17704).

The ssRNA 2'-O-methyltransferase enzymes are the ones which normally use (or is capable of using) S-adenosyl-L-methionine (SAM or AdoMet) as a co-factor (Huang, (2012) Biochemistry 51, 4087-4095).

The biogenesis of animal piRNAs as well as plant miR-NAs and siRNAs involves their modification at the 3'-termini (Kim et al., (2010) Cell 143, 703-709). In animals this reaction is carried out by a family of single-stranded RNA 2'-O-methyltransferases which share a conservative catalytic domain with plant and bacteria RNA modifying enzymes. Human and D. melanogaster ssRNA 2'-O-methyltransferases, piRMTs, catalyzes methyl group transfer from S-adenosyl-L-methionine to piRNA (Saito et al., (2007) Genes Dev. 21, 1603-1608). Unlike plant methyltransferases which display a strong preference towards duplex RNAs and efficiently methylates both strands of it (Vilkaitis et al., (2010) RNA 16, 1935-1942), these animal homologues modify single-stranded RNA substrates of 21-38 nt in length (Saito et al., (2007) Genes Dev. 21, 1603-1608). This methylation is critical for piRNA stability and function (Horwich et al., (2007) Curr Biol. 17, 1265-1272).

The RNA 2'-O-methyltransferase enzyme to be used in the method described herein may be obtained from animals and is preferably Hs-piRMT (acquired from human) or Dm-piRMT (obtainable from a fruit fly), a catalytic domain of piRMT or a piRMT homolog (or a catalytic domain thereof), such as mouse piRMT (Kirino and Mourelatos, (2007) RNA 13, 1397-1401). The sequences of the wild type Hs-piRMT and Dm-piRMT can be found in GenBank, Accession Nos NP_653185.2 and NP_610732.1, respectively. The protein sequences are as follows:

```
SEQ ID No: 1 Hs-piRMT:
MEENNLQCSSVVDGNFEEVPRETAIQFKPPLYRQRYQFVKNLVDQHEP

KKVADLGCGDTSLLRLLKVNPCIELLVGVDINEDKLRWRGDSLAPFLG

DFLKPRDLNLTITLYHGSVVERDSRLLGFDLITCIELIEHLDSGDLAR

FPEVVFGYLSPSMIVISTPNSEFNPLFPSVTLRDSDHKFEWTRMEFQT

WALYVANRYDYSVEFTGVGEPPAGAENVGYCTQIGIFRKNGGKATESC

LSEQHDQHVYKAVFTTSYPSLQQERFFKLVLVNEVSQQVESLRVSHLP

RRKEQAGERGDKPKDIGGSKAPVPCFGPVFTEVEKAKIENSPTPFCVG

DKFFVPLQRLLAYPKLNRLCANEEMMRSVIADSIPLSSDGSAVVADLR

NYFDEQFEF

SEQ ID No: 2 Dm-piRMT:
MFSHKFICGSLTKMTETGITFDPPVYEQRYCATIQILEDARWKDQIKK

VVEFGCAEMRFFQLMRRIETIEHIGLVDIDKSLLMRNLTSVNPLVSDY

IRSRASPLKVQILQGNVADSSEELRDTDAVIAIELIEHVYDDVLAKIP

VNIFGFMQPKLVVFSTPNSDFNVIFTRFNPLLPNGFRHEDHKFEWSRD

EFKNWCLGIVEKYPNYMFSLTGVGNPPKEYESVGPVSQIAIFVRKDML

EMQLVNPLVSKPNIDKESIPYKLIHTVEYPFYVDTRTEKEKLWTEVQI

ELQRFKRQFESSEIEEGTYQDTCNMPIAFLLDRLEHVGATKERIEELL

LENNLTVENECVLIVSSDQESEWSDPYKFSDRSSQDDALVDQEQEEER

WDQGPES
```

Preferably the ssRNA 2'-O-methyltransferase enzyme has at least 70% sequence identity, more preferably at least 80% sequence identity, most preferably at least 90% sequence identity with SEQ ID No: 1 or SEQ ID No: 2.

The RNA 2'-O-methyltransferase enzyme to be used in the method described herein may also be an engineered (modified, truncated or enlarged) version of the natural proteins which retains the majority of their catalytic domain. The catalytic domains of Hs-piRMT and Dm-piRMT comprise aa 22-280 of SEQ ID NO: 1 and 16-291 of SEQ ID NO: 2 respectively.

The RNA 2'-O-methyltransferase enzyme to be used in the method described herein may also be obtained from bacteria, archaea and viruses, which could be identified by their AdoMet-dependent ssRNA 2'-O-methyltransferase activity and which belong to the superfamily of "S-adenosyl-L-methionine-dependent methyltransferases" (http://supfam.org/SUPERFAMILY/cgi-bin/scop.cgi?sunid=53335) as defined in the Superfamily database of the HMM library and genome assignment server (http://supfam.csbrisac.uk/SUPERFAMILY/).

RNA

In the method described herein the RNA which is modified is a single-stranded molecule. In particular, the RNA strand is not an animal piRNA 2'-O-methylated at 3' terminal nucleotide.

The RNA strand is preferably a strand of a virus, a microorganism, a plant or an animal (including human) as long as it has an unmethylated 3' terminal 2'-OH group. Accordingly, the method of invention can comprise an additional step of obtaining or providing a strand of RNA from a biological sample taken from a virus, a microorganism, a plant or an animal (including human).

The RNA strand may span the range of 20-81000 nucleotides in length, corresponding accordingly to the shortest ssRNA modified by piRMT and the longest coding sequence in human genome (the titin gene); it is preferably, 20-400 nt in length, which corresponds accordingly to the shortest ssRNA modified by Hs-piRMT and the size of largest bacterial ssRNAs; most preferably it is 22-80 nt in length as shown in Example 2 below.

The single-stranded RNA that can be modified using the method of invention may be eukaryotic long non-coding RNA, small non-coding RNA, such as miRNA, siRNA, piRNA; bacterial small regulatory RNA; viral RNA; mRNA, or synthetic ssRNA.

In one embodiment of the invention the strand of RNA is miRNA, siRNA or piRNA. Preferably the miRNA, siRNA or piRNA is from a biological sample taken from an animal (e.g. human) or plant. Preferably the strand of RNA is 21-36 nt in length. Preferably the strand of RNA has an unmodified 2'-OH group at 3' terminal nucleotide.

In another embodiment of the invention the strand of RNA is sRNA. Preferably the sRNA is from a biological sample taken from bacteria. Preferably the sRNA is 50-400 nt in length.

In general, this method is suitable for ssRNAs from all organisms with the exception to the ones with 2'-O-modifications at their 3' terminal nucleotides.

Co-Factor

The co-factor for use in the methods described herein is based on the molecule S-adenosyl-L-methionine (SAM or AdoMet) and is an S-adenosyl-L-methionine analog which comprises a functional group or a reporter group in an extended side-chain, which can be transferred onto the ssRNA by the enzyme described above.

In particular, the AdoMet analog may have the following formula:

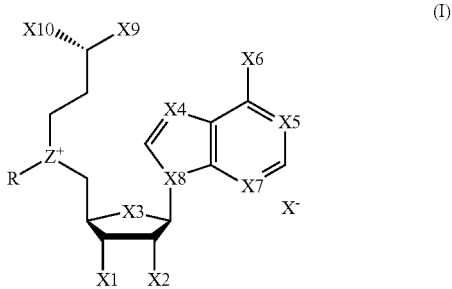

(I)

$X_1$ and $X_2$ represent —OH, —SH, —H or —F;

$X_3$ represents —O—, —NH—, —CH$_2$—, —S—, or —Se—;

$X_4$, $X_5$, $X_7$, $X_8$ represent —N—, or —CH—;

$X_6$ represents —NH$_2$, —OH, —OCH$_3$, —H, —F, —Cl, —SH or —NHCH$_3$;

$X_9$ represents —CO$_2$H, —PO$_3$H, —H, —CHO, —CH$_3$, or —CH$_2$OH;

$X_{10}$ represents —NH$_2$, —OH, —H, —CH$_3$, or —NHCH$_3$;

X⁻ is an organic or inorganic anion selected from trifluoroacetate, formate, halide and sulfonate;

Z represents S or Se;

C-bound H atoms in the adenosine moiety can be replaced by —F, —OH, —NH$_2$, or —CH$_3$;

R is an extended side-chain comprising a functional group or a reporter group.

Preferably R comprises a —CH=CH—, —C≡C— or —C(=O)— in a β-position to Z+ centre and is separated there from it by CR1R2-, where R1 and R2 are independently H or D.

Suitable co-factors comprising functional groups and reporter groups are also described in WO 2006/108678.

Figure 2:
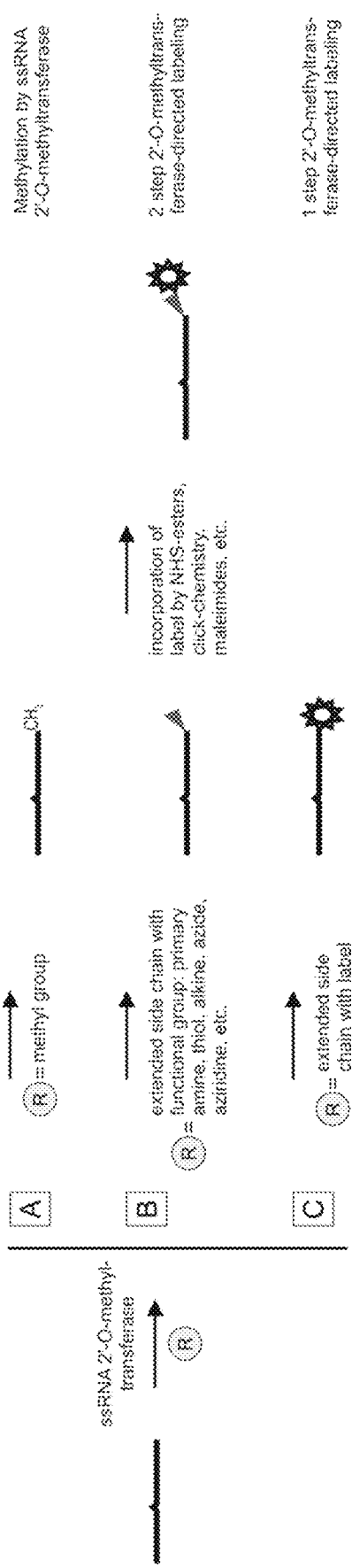
FIG. 2 shows strategies of Dm-piRMT and Hs-piRMT-directed labeling of ssRNAs in embodiments of the invention in comparison to the natural reaction. Pathway A (top) highlights the natural piRMT reaction—the methyl group transfer from S-adenosyl-L-methionine towards single-stranded RNA (R=methyl). Pathway B (center) describes a two step labeling strategy thereby a functional group (primay amine, thiol, alkine, azide, aziridine, carboxyl, aromatic hydrocarbon, etc.) embedded in the side chain R of a synthetic cofactor is transfered to the 3' end of ssRNA and then the functional group is used to attach a desired reporter group in a second step. An alternative strategy C (bottom) illustrates one-step labeling of RNA molecules by direct piRMT-dependent transfer of a reporter group (e.g., biotin, fluorofores, etc.) embedded in the side chain R of a cofactor analog. The triangles represent functional groups, stars—reporter groups.

The use of a co-factor comprising a functional group or a reporter group allows for the labeling of ssRNA via two different strategies, Pathway B and Pathway C shown in FIG. 2. Pathway A (top) illustrates the natural RNA 2'-O-methyltransferase reaction—the methyl-group transfer from S-adenosyl-L-methionine towards single-stranded RNA (R=methyl). Pathway B (centre) describes a two-step RNA labeling strategy whereby a functional group (primary amine, thiol, alkine, azide, aziridine, carboxyl, aromatic hydrocarbon, etc.) embedded in the side chain of a synthetic AdoMet analog is transferred to the 3'-end of ssRNA and then the functional group is used to attach a desired reporter group in a second step. An alternative strategy C (bottom) depicts one-step labeling of RNA molecules by direct RNA 2'-O-methyltransferase-dependent transfer of a reporter group (e.g., biotin, fluorofores, etc.) embedded in the side chain R of a cofactor analog.

Accordingly, where the co-factor comprises a functional group, this must be capable of being used to attach a desired reporter group in a second step. In this embodiment the method of the invention may comprise a further step of reacting the functional group attached to the ssRNA with a compound comprising a reactive group (or second functional group) attached to a reporter group under conditions which allow for the transfer of the reporter group onto the ssRNA.

The functional group comprises a reactive group (group X) which may comprise an amino group, a thiol group, a hydrazine group, a hydroxylamine group, a 1,2-aminothiol group, an azide group, a diene group, an alkyne group, an arylhalide group, a terminal silylalkyne group, an N-hydroxysuccinimidyl ester group, a thioester group, an isothiocyanate group, an imidoester group, a maleimide group, a haloacetamide group, an aziridine group, an arylboronic acid group, an aldehyde group, a ketone group, a phosphane ester group, a dienophile group, or a terminal haloalkyne group.

Group X can then be reacted with a compound comprising a second reactive group (group Y) which is attached to the reporter group. Suitable groups for X and Y, and the subsequent linkage which the reaction forms between the ssRNA and the reporter group are shown below in Table 1. Suitable reporter groups are a fluorophore, a quantum dot, an oligonucleotide, a DNA aptamer, a RNA aptamer, a ribozyme, DNA with specific protein targets or sequences for analysis (bar codes), an affinity tag, an antibody, a peptide, a protein, a glycan or a nanoparticle.

TABLE 1

Mutually reactive functional groups X and Y suitable for conjugation

| Reactive group X or Y | Reactive group Y or X | Linkage formed |
| --- | --- | --- |
| Primary amine | N-hydroxysuccinimidyl ester | amide |
| Primary amine | thioester | amide |
| Primary amine | isothiocyanate | thioureas |
| Primary amine | imidoester | imidate |
| Primary amine | aldehyde, ketone | imine/secondary amine after reduction |
| Thiol | maleimide | thioether |
| Thiol | haloacetamide | thioether |
| Thiol | aziridine | thioether |
| Thiol | thiol | disulfide |
| Hydrazine | aldehyde, ketone | hydrazone |
| Hydroxylamine | aldehyde, ketone | oxime |
| 1,2-Aminothiol | aldehyde, ketone | thiazolidine |
| 1,2-Aminothiol | thioester | amide |
| Azide | alkyne | 1,2,3-triazole |
| Azide | phosphane ester | amide |
| Diene | dienophile | cyclohexene |
| Terminal alkyne | arylhalide | arylalkyne |
| Arylhalide | arylboronic acid | biaryl |
| Terminal silylalkyne | terminal haloalkyne | diyne |

The functional group of the co-factor may optionally be in protected form, such as a protected amino group, a protected thiol group, a protected hydrazine group, a protected hydroxyamino group, a protected aldehyde group, a protected ketone group and a protected 1,2-aminothiol group. As such, the reactive group X may be first transferred from the co-factor to the ssRNA in a protected form as a derivative that is converted to an active functional form in a separate step. For example, thiols may be transferred with acetyl protecting group (protected F1=—S—COCH$_3$) which can be readily removed to yield thiol (F1=—SH) by treatment of modified DNA with 20% ammonia, or transferred 1,2-diol can be converted to aldehyde by oxidation with sodium periodate.

Alternatively, in a one-step labeling procedure the extended side-chain R of the AdoMet analog comprises a reporter group. Suitable reporter groups include a fluorophore, a quantum dot, an affinity tag, an oligonucleotide primer, a DNA aptamer, an RNA aptamer, ribozymes, or DNA with specific protein targets or sequences for analysis (bar codes). The affinity tag may be biotin, maltose, c-myc-tag, HA-tag, digoxygenin, flag-tag, dinitrophenol, His tag, strep-tag, glutathione, or nickel-nitrilotriacetic acid (NTA).

Analysis Methods

As indicated above, methods of the present invention has particular utility in analysis of the small single-stranded RNAs in biological samples, including the determination of the types of small RNAs present in a particular sample, and the exploration and discovery of new species of small ssRNAs within the small RNAs transcriptome in biological samples. Accordingly, the method described above can further comprise steps of using the reporter groups or functional groups to enrich, to clone and/or to sequence the RNA strand, to detect or quantitate the small ssRNAs.

In particular, the method of the present invention can be used in the analysis of single-stranded RNAs in a biological sample. Accordingly, all of the methods described herein may comprise a step of obtaining and/or preparing a biological sample. In particular, the biological sample can be individual cells, cultured cells, tissues (highly differentiated, fetal), biopsy, bodily fluids (e.g. blood, urine, tears, saliva), whole organisms (e.g. plants), bacterial strains or viruses. Methods of preparing such samples, so that they are suitable for analysis of the ssRNAs they contain, are known in the art.

Figure 7:
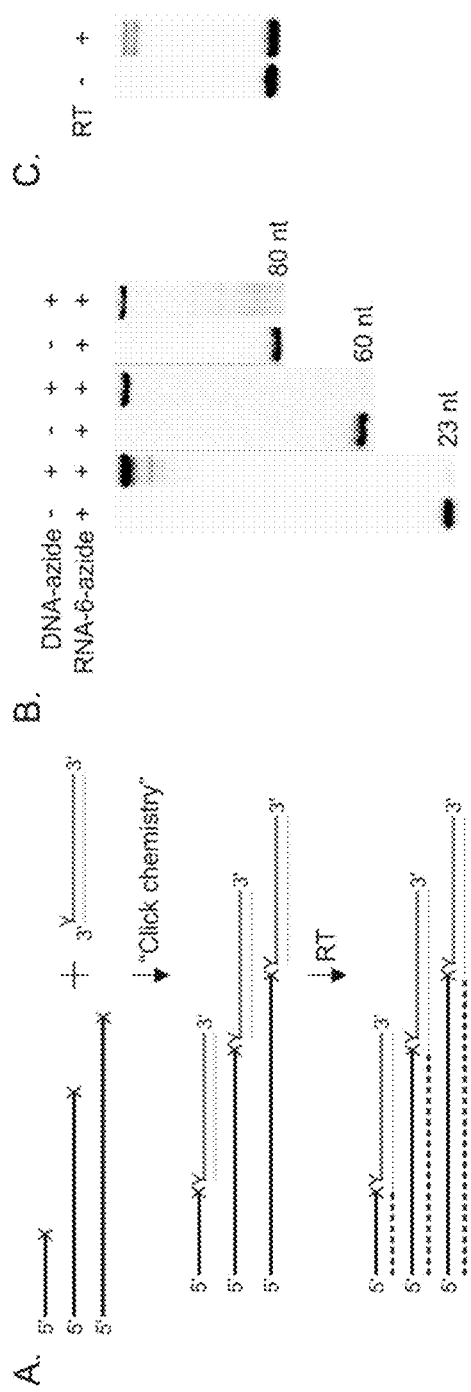
FIG. 7 shows that piRMT modified RNA can be further used for its sequencing through DNA oligonucleotide attachment and subsequent reverse transcription. A. Scheme showing ligation independent strategy for RNA sequencing. At least 22-80 nt long RNAs (black lines) can be modified by Dm-piRMT with, for example 6-azide (X), as shown in FIG. 6, then through "click chemistry" attached to terminal alkyne (Y) modified double-stranded DNA oligonucleotides (gray and light gray lines) and reverse transcribed to complementary DNAs (dotted black line). B and C. The proof of concept laid down in FIG. 7A. B. DNA-alkyne can be successfully attached to Dm-piRMT generated RNA-6-azide. For click reaction 10 µM of alkylated DNA was mixed with 10 µM $^{32}$P-labeled modified RNA, ~60% DMSO and 3.3 mM CuBr-TBTA (3.3 mM CuBr, 3% DMSO, 7 mM TBTA). After 1 h of incubation at 45° C. samples were analyzed in 13% PAG. C. New DNA strand, complementary to RNA of interest, can be synthesized from RNA-DNA hybrid. After click reaction 0.08 µM of RNA-DNA conjugate were reverse transcribed by 10 u/µl of RevertAid RT (RT) (Thermo Scientific) in reaction mixture containing 0.4 mM dNTP, 1 u/µl RiboLock (Thermo Scientific) and 1× RevertAid RT reaction buffer at 30° C. for 2 h 10'.
Figure 8:
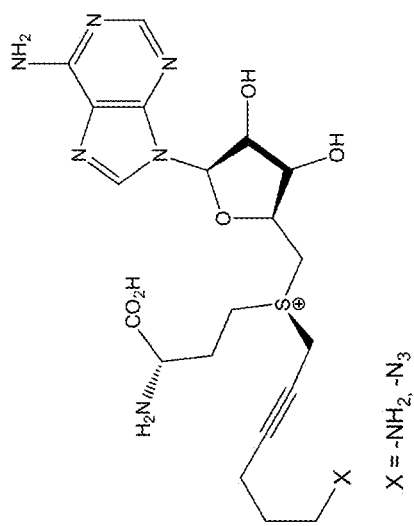
FIG. 8 shows the structure of example co-factor molecules applicable for two step labeling: X=Ado-6-amine and X=—N$_3$-Ado-6-azide.
Figure 9:
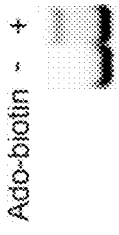
FIG. 9 shows polyacrylamide gel analysis of Dm-piRMT-dependent labeling of ssRNA in a single step as depicted in FIG. 2C. The biotinylation of single-stranded miR173.1 was performed as described in FIG. 3 with the exception that 2 µM of Dm-piRMT was used in the modification reaction and no NaIO$_4$/β-elimination was applied.

In a particular embodiment the method of the present invention is used to examine the small single-stranded RNA pool from a biological sample by the strategies shown in FIGS. 7 and 9: ssRNA 2'-O-methyltransferase-dependent alkylation to attach affinity reporter (e.g. biotin) for selective enrichment and cloning (FIG. 9, strategy A) or RNA 2'-O-methyltransferase-dependent alkylation to attach an oligonucleotide adapter for primed reverse transcription and sequencing (FIG. 7, strategy B).

This method of strategy A can comprise the steps of:
(a) labeling the 3' end of ssRNA in the biological sample using the methods described above to attach an affinity group;
(b) affinity binding and enrichment of the labeled ssRNA; and
(c) cloning and sequencing of the enriched ssRNAs.

The method of strategy B can comprise the steps of
(a) attaching a functional group to the 3' end of ssRNA in the biological sample using the methods described above;
(b) reacting the functional group with a reactive group attached to an oligonucleotide under conditions that allow for the transfer of the oligonucleotide onto the 3' end of the ssRNA;
(c) sequencing the ssRNA using the oligonucleotide.

To the extent that the ssRNA 2'-O-methyltransferase modifies only at 3' terminal nucleotide 2'-OH group unmethylated ssRNAs, the results of (massive parallel) sequencing would be free of DNA contamination, enable the differentiation between modified and unmodified RNAs as well as among circular, single or double-stranded RNAs.

The methods of the invention involve ssRNA 2'-O-methyltransferase dependent modification of RNA molecules, exceptionally, and their further use for enrichment, cloning and/or sequencing. As ssRNA specific modification can be fulfilled even in DNA containing samples, the amount of steps comprising ssRNA purification for analysis (e.g. DNA elimination) can be reduced. This leads to smaller losses of ssRNA sample as well as allows starting with smaller amounts of it. This approach can be particular beneficial for analysis of ssRNA in biological samples where its concentrations are exceptionally low, such as bodily fluids (Sterling et al., (2014) Nucleic Acids Res., epub July 23).

The methods of the present invention encompasses analysis of the the modification status of the 3' terminal nucleotide 2'-OH group in ssRNAs. As 2'-O-methylated RNA is a product of ssRNA 2'-O-methyltransferase modification reaction, it cannot be used as substrate. Such a method to specifically identify the 2'-O-unmethylated ssRNAs can be applied to pathology identification in animal (e.g. human) germline cells, where piRNAs are normally methylated, or plants, where all small ssRNAs appear to be modified under normal conditions (Lozsa eta la., (2008) Nucleic Acids Res. 36, 4099-4107). In these cases, the detection of unmethylated ssRNAs and their identification would serve both as an indicator of disease and a target for treatment.

The methods of this invention can be applied for detection and analysis of a newly identified class of non-coding RNAs, circular RNAs (circRNAs) (Salzman et al., (2012) PLoS ONE 7, e30733). circRNAs are proposed to act as miRNA sponges in eukaryotes in this way controlling the amount of active miRNA molecules and, to higher extent, the physiology of whole organism (Kosik, (2013) Nature 495, 322-324). Up to date circRNAs are determined by comparing RNAse R and mock treated samples with the intent that in exonuclease treated samples only circRNAs should be left (Jeck et al., (2013) RNA 19, 141-157). The main drawbacks of this approach are the following: (1) considerable amount of material is needed for two different samples' preparation, (2) exonuclease in use is unable to eliminate lariat RNAs, which later hampers the analysis.

Based on our invention the method for circRNA identification and analysis can be comprised of subsequent steps:
a) removal and analysis of single-stranded RNAs: labeling of ssRNAs, including free 3' ends containing lariat RNAs; affinity binding and enrichment of labeled RNAs; cloning and sequencing of enriched RNA strands;
b) analysis of circRNAs left in the sample: linearization of circRNAs, their modification and sequencing.

The method described, contrary to the currently applied ones, enables parallel analysis of single-stranded and circRNAs. In addition to this, it separates lariat RNAs and linear transcripts with scrambled exons from circRNAs facilitating true circular RNA identification.

The present invention involving ssRNA 2'-O-methyltransferases' catalyzed modification of ssRNAs may be an adequate alternative to 3' adapter ligation and to T4 RNA ligases, in particular. As sequencing methods are struggling with adapter ligation during RNA library preparation, this invention presents an alternative method for 3' adapter attachment, in particular—2'-OH modification of a 3' terminal nucleotide in RNA strand with a functional group followed by 3' adapter addition using a click chemistry reaction (FIG. 7). This method circumvents inefficient, RNA sequence dependent and DNA as well as 2'-O-methylated RNA indiscriminatory 3' adapter ligation step in RNA library preparation (Raabe et al., (2013) Nucleic Acids Res. 42, 1414-1426). Combined with techniques of CircLigase based approaches (Jackson et al., (2014) BMC Genomics 15) our method can fully liberate RNA library preparation from adapter ligation.

As methods of the invention involve the modification of 3' termini of ssRNAs they can be applied for precise determination of ssRNA sequence from 3' end. 70% of human genes are characterized by alternative poliA sites which lead to different isoforms of transcripts with variable length and sequence of their 3' untranslated regions (UTRs) (Xia et al., (2014) Nat Commun. 5, 5274). As 3'UTRs bear complementary sequence motifs for miRNAs, these sites are affected due to alternative polyadenilation (APA). As specific APA events are tumor specific, their identification holds potential for prognostic use. Using the methods of the invention miRNA detection and precise 3' termini identification of mRNA can be combined to one powerful tool.

Methods of the invention allow the detection of cellular small non-coding RNAs, whose expression level is affected in response to a treatment or environmental conditions.

The detection of the attached reporter on the ssRNA can be achieved by the emission of fluorescence, or assays specific for the reporter group being used (e.g. avidin or streptavidin conjugated to peroxidase or alkaline phosphotase, antigens, aptamers, color-codes tiny beads—microsphere particles, beads etc).

The present invention allows the development of tools for clinical diagnostics based on simultaneous quantitation of all types of ssRNAs.

ssRNA 2'-O-methyltransferase-dependent RNA labeling allows developing a set of tools for research and clinical applications: analysis and detection in fluid systems, solid substrates, in situ, by confocal fluorescence microscopy, etc.

Kit

In a further aspect the present invention provides a kit for use in labeling a ssRNA comprising (a) a co-factor comprising a reporter group or a functional group; and (b) an ssRNA 2'-O-methyltransferase capable of transferring the reporter group or the functional group onto the ssRNA.

Each element of the kit is in a separate container.

The kit may optionally further comprise instructions for using the components of the kit in order to label a ssRNA. The instructions are provided on an appropriate medium, for example paper or an electronic data carrier.

The description herein regarding the methods of the present invention also applies to the elements of the kit of the invention.

The present invention will now be described in further detail, by way of example only, with reference to the following Examples and related Figures.

EXAMPLES

Example 1. Efficient Methylation of the 3'-Nucleotide of Short ssRNA

Figure 3:
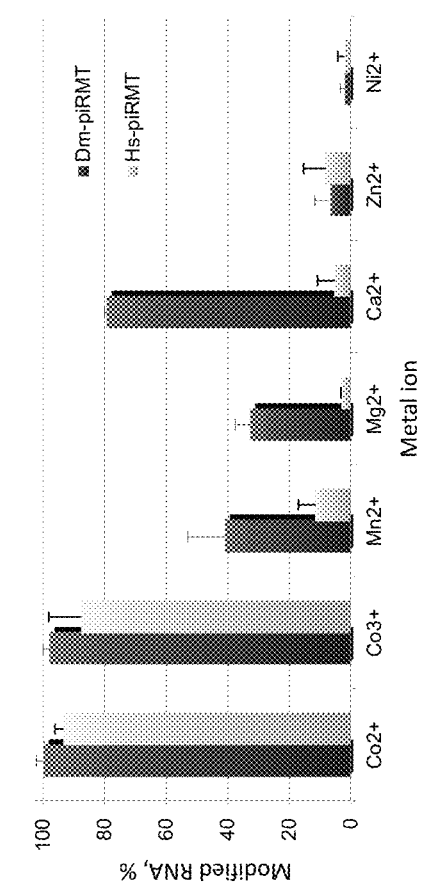
FIG. 3 shows the metal ion requirements of Dm-piRMT and Hs-piRMT for efficient catalysis. A. From all analyzed potential metal ion cofactors, only the presence of $Co^{2+}$ or $Co^{3+}$ in the reaction mixture confers full methylation of ssRNA substrate. To test the requirement of different metal cofactors, 20 µl reaction volumes, containing reaction buffer [10 mM Tris-HCl (pH 7.4), 50 mM NaCl, 0.1 mg/ml BSA, 5% (v/v) glycerol and 0.05 u/µl RiboLock (Thermo Scientific)], 0.2 µM $^{32}$P-labelled miR173.1 (5'-UUCGC-UUGCAGAGAGAAAUCAC-3', 22 nt) (SEQ ID NO: 3), 0.1 mM AdoMet, 10 mM metal ion and 1 µM of piRMT proteins' were mixed. After 30 min of incubation at 37° C., the degree of modification was determined by $NaIO_4/\beta$-elimination reaction, during which RNA was treated with 0.2 mM $NaIO_4$ in borax/boric acid buffer [0.06 M, pH 8.6] for 15 min followed by 75 min incubation in borax/boric acid buffer II [0.06 M pH 9.6] at 42° C. Reaction samples were analyzed in 13% denaturing polyacrylamide gel (PAG) and autoradiographed. Fractions of methylated RNA, represented by bands with lower electrophoretic mobility, were evaluated using Multi Gauge version 3.0 software (Fujifilm). The depletion of metal ions by EDTA in the reaction mixture, together with the sample without any metal cofactor added, further confirms that the effective piRMT methylation is due to $Co^{2+}$ and $Co^{3+}$ ions. B. Column-diagram of RNA methylation efficiency with different metal cofactors. Results are average of duplicate experiments±S.D.
Figure 3:
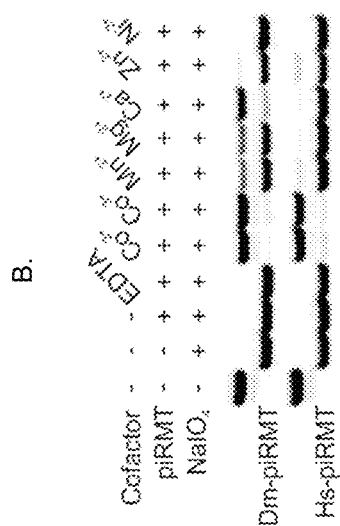
Figure 4:
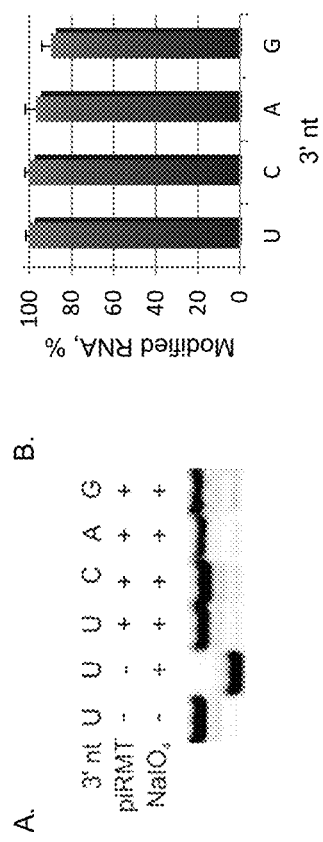
FIG. 4 shows improved uniformity of modification efficiency towards different terminal nucleotides in ssRNA substrates. The use of $Co^{2+}$ as metal cofactor results in equally effective modification of RNA substrates with different 3' terminal nucleotides by Dm-piRMT, while it is known, that other homologous piRNA methyltransferase, for example mouse piRMT, have a preference to A over C, U and G. A. RNA modification experiments were performed as described in FIG. 3, with the exception, that miR173.1 with different 3' terminal nucleotides, namely U, C, A and G, was used as substrate and 2 µM of Dm-piRMT was added to the reaction mixtures. B. Column-diagram of modification efficiency of miR173.1 with different 3' terminal nucleotides. Results are average of two experiments±S.D.

The results of Example 1 are shown in FIGS. 3 and 4, which demonstrate metal ion dependency and reaction conditions permitting uniform modification of different 3' terminal nucleotides of piRMT-dependent methylation of single-stranded RNA substrate (miR173.1 strand) resembling plant natural miRNA.

Example 2. piRMT-Dependent Alkylation and Labeling of ssRNA

Figure 5:
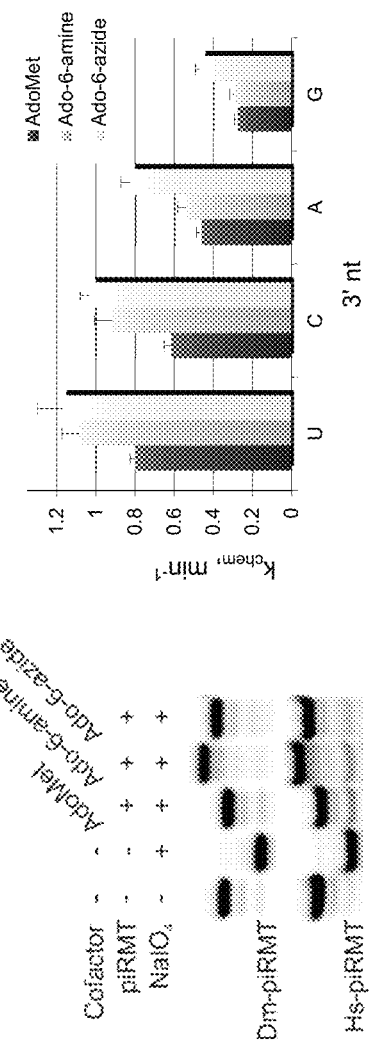
FIG. 5 shows that Dm-piRMT and Hs-piRMT can be used to effectively transfer various functional groups from synthetic cofactor analogues to ssRNA. A. ssRNA 2'-O-methyltransferases covalently modify the miR173.1 strand. Reactions were performed using 2 µM of piRMT methyltransferases and AdoMet or synthetic cofactor analogues, Ado-6-amine or Ado-6-azide, with extended side chains for two step labeling. All the experimental details are given in FIGS. 3 and 4. B. Dm-piRMT modifies RNA substrates with different 3' terminal nucleotides with synthetic cofactor analogues at the same or even higher reaction rates ($k_{chem}$, min$^{-1}$) as compared to AdoMet. To measure the rate of modification reactions, 0.2 µM $^{32}$P-labelled miR173.1 with different 3' terminal nucleotides, 0.1 mM AdoMet or its synthetic analogues, 10 mM Co$^{2+}$ and 2 µM of Dm-piRMT were added to the reaction buffer [10 mM Tris-HCl (pH 7.4), 50 mM NaCl, 0.1 mg/ml BSA, 5% (v/v) glycerol and 0.05 u/µl RiboLock (Thermo Scientific)] and incubated at 37° C. At a certain time points reactions were stopped by the addition of Proteinase K in stop buffer [7 mM Tris-HCl (pH 7.4), 0.17 mM EDTA, 3 mM NaCl and 0.5% SDS] to a final concentration of 0.4 mg/ml and further incubation at 55° C. for 20 min. This was followed by NaIO$_4$/β-elimination reaction and denaturating PAG electrophoresis described in FIG. 3. Results are mean of two experiments±S.D.
Figure 6:
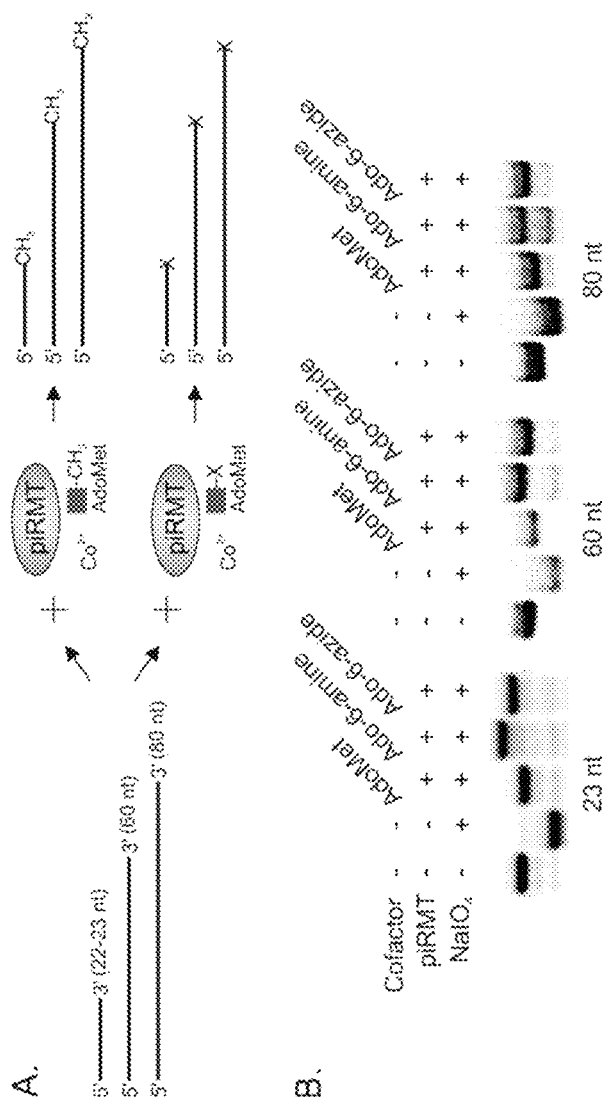
FIG. 6 shows that in the presence synthetic cofactor analogues Dm-piRMT can alkylate RNA substrates of a wide length range. A. Principal scheme of 22-80 nt long RNA modification by Dm-piRMT with methyl group (CH$_3$) or extended side chains (X) from AdoMet or synthetic cofactor analogues (AdoX), respectively. B. The proof of concept delineated in FIG. 6A. Experiments were prepared as described in FIG. 3, except that 2 µM of Dm-piRMT was used. The 23 nt long RNA substrate was siR173.1 (5'-UUAACGCUUGCAGAGAGAAUCAC-3') (SEQ ID NO: 4). The same siR173.1 sequence was at the 3' ends of 60 and 80 nt long RNA molecules.

In FIGS. 5-7 it is demonstrated that piRMT-mediated coupling of side chains on single-stranded RNA is appropriate for two-step labeling through primary amine from Ado-6-amine. Experiments using 0.2 µM synthetic 22-80 nt long single-stranded RNA, radiolabeled with phosphorus-33 isotope, were performed for 30' at 37° C. with 100 µM synthetic cofactor either in the presence of 2 µM piRMT or in the absence of protein (FIGS. 5 and 6). The samples were resolved on 13% denaturing polyacrylamide gel (with 7M urea).

In FIG. 7 it was demonstrated, that piRMT generated RNA-6-azide can be attached to DNA-alkyne (B) and copy DNA can be transcribed from this RNA-DNA conjugate for RNA sequencing (C).

In FIG. 9 the piRMT-dependent direct labeling of short RNA strands with Ado-biotin is highlighted

---

The invention claimed is:

1. A method for modifying a strand of single-stranded RNA (ssRNA strand) at the 3' end, said method comprising contacting the ssRNA strand with a ssRNA 2'-O-methyltransferase in the presence of a co-factor, under conditions which allow for the transfer by the ssRNA 2'-O-methyltransferase of a part of the co-factor onto the 3' end of the ssRNA strand to form a modified ssRNA strand, wherein the ssRNA strand bears unmethylated 2'-OH group at 3' terminal nucleotide and wherein the part of the co-factor transferred comprises more than 4 atoms and contains a reporter group or a functional group capable of being used to attach a reporter group.

2. A method according to claim 1 wherein the ssRNA strand is 20 to 81000 nucleotides in length.

3. A method according to claim 1 wherein the ssRNA strand is eukaryotic long non-coding RNA and small non-coding RNA.

4. A method according to claim 1 wherein the ssRNA 2'-O-methyltransferase comprises an amino acid sequence having at least 70% sequence identity with SEQ ID No: 1 or SEQ ID No: 2.

5. A method according to claim 1 wherein the co-factor is an S-adenosyl-L-methionine analogue.

6. A method according to claim 1 wherein the co-factor comprises a functional group selected from the group consisting of an amino group, a thiol group, a hydrazine group, a hydroxylamine group, a 1,2-aminothiol group, an azide group, a diene group, an alkyne group, an arylhalide group, a terminal silylalkyne group, an N-hydroxysuccinimidyl ester group, a thioester group, an isothiocyanate group, an imidoester group, a maleimide group, a haloacetamide group, an aziridine group, an arylboronic acid group, an aldehyde group, a ketone group, a phosphane ester group, a dienophile group and a terminal haloalkyne group.

7. A method according to claim 1 wherein the co-factor comprises a functional group and the method further comprises a step of reacting the functional group with a compound comprising a reporter group under conditions which allow for the transfer of the reporter group to the ssRNA strand.

8. A method according to claim 1 wherein the reporter group is selected from the group consisting of a fluorophore, a quantum dot, an affinity tag, an oligonucleotide, a DNA aptamer, an RNA aptamer, a DNAzyme, an RNAzyme, an antibody, a peptide, a protein, a glycan, a nanoparticle, and a magnetic particle.

9. A method according to claim 8 wherein the affinity tag is biotin, c-myc-tag, HA-tag, digoxygenin, flag-tag, dinitrophenol, His-tag, strep-tag, glutathione, nickel-nitrilotriacetic acid (NTA), or maltose.

10. A method according to claim 1 wherein the part of the co-factor transferred comprises the functional group capable of being used to attach a reporter group and the method further comprises a step of reacting the functional group with a reactive group attached to an oligonucleotide under conditions that allow for the transfer of the oligonucleotide onto the 3' end of the ssRNA strand.

11. A method according to claim 10 wherein said functional group is azide, and said reactive group is alkyne.

12. A method according to claim 10, wherein the method further comprises a step of sequencing the ssRNA strand through DNA oligonucleotide attachment and reverse transcription.

13. A method according to claim 1, wherein the contacting is in a reaction mixture to which divalent Co2+ or trivalent Co3+ ions are added.

14. A method according to claim 1 comprising an additional step of providing the ssRNA strand from a sample taken from a virus, microorganism, animal or plant.

15. A method for analysing ssRNA present in a biological sample, said method comprising:
    (a) attaching a reporter group to the 3' end of an ssRNA strand in the biological sample using the method of claim 1;
    (b) analysing the reporter group attached to the ssRNA strand.

16. A method according to claim 15 wherein the reporter group is an affinity tag and step (b) comprises affinity binding and enrichment of the ssRNA strand attached to the affinity tag.

17. A method according to claim 16 further comprising the steps of cloning the enriched ssRNA strand and then sequencing said ssRNA strand.

18. A method according to claim 15 wherein step (b) comprises detecting and quantifying the reporter group attached to the ssRNA strand.

* * * * *